(12) United States Patent
Aggerholm et al.

(10) Patent No.: US 10,086,179 B2
(45) Date of Patent: Oct. 2, 2018

(54) MEDICAL BALLOON

(71) Applicant: Cook Medical Technologies LLC, Bloomington, IN (US)

(72) Inventors: Steen Aggerholm, St. Heddinge (DK); Tue Thuren Bödewadt, Solroed Strand (DK); Thomas Lysgaard, Solroed Strand (DK); David A. Drewes, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 312 days.

(21) Appl. No.: 15/077,533

(22) Filed: Mar. 22, 2016

(65) Prior Publication Data

US 2016/0199623 A1   Jul. 14, 2016

Related U.S. Application Data

(63) Continuation of application No. 13/794,972, filed on Mar. 12, 2013, now Pat. No. 9,327,102.

(30) Foreign Application Priority Data

Mar. 27, 2012   (GB) .................................. 1205369.0

(51) Int. Cl.
*A61M 29/00* (2006.01)
*A61M 25/10* (2013.01)
(Continued)

(52) U.S. Cl.
CPC ......... *A61M 25/104* (2013.01); *A61L 29/041* (2013.01); *A61L 29/049* (2013.01);
(Continued)

(58) Field of Classification Search
CPC ....... B29C 49/04; B29C 49/22; B29C 49/786; A61M 25/1029; A61M 2025/1075
See application file for complete search history.

(56) References Cited

U.S. PATENT DOCUMENTS 5,620,649 A   4/1997   Trotta
6,143,416 A   11/2000  Brindle et al.
(Continued)

FOREIGN PATENT DOCUMENTS

EP    0 745 395 A2      12/1996
WO    WO 99/12585 A2    3/1999
WO    WO 2009/080320 A1 7/2009

OTHER PUBLICATIONS

Communication from EPO with European Search Report and Annex for corresponding European Patent Application No. EP 1 13 27 5052, dated Aug. 13, 2013, 8 pgs.
(Continued)

*Primary Examiner* — Robert Lynch
(74) *Attorney, Agent, or Firm* — Brinks Gilson & Lione

(57) ABSTRACT

A medical balloon for a balloon catheter is described. The balloon has at least a first layer made from a first material and a second layer made from a second material, said first and second layers being in overlying relationship with one another and being integral with one another; wherein the first layer has a softening or melting temperature which is higher than a softening or melting temperature of the second layer. A method of forming the medical balloon is also described, including locating a raw tubing in a mold; preheating and inflating the raw tubing so as to cause it to stretch; heating the raw tubing to soften or melt the second layer; setting the inflated raw tubing to form the medical balloon; and cooling the set balloon.

13 Claims, 5 Drawing Sheets

(51) Int. Cl.
A61L 29/04 (2006.01)
A61L 29/06 (2006.01)
B29C 49/04 (2006.01)
B29C 49/22 (2006.01)
B29C 49/78 (2006.01)
A61L 29/18 (2006.01)
B29L 31/00 (2006.01)

(52) U.S. Cl.
CPC .............. *A61L 29/06* (2013.01); *A61L 29/18* (2013.01); *A61M 25/1029* (2013.01); *B29C 49/04* (2013.01); *B29C 49/22* (2013.01); *B29C 49/786* (2013.01); *A61M 2025/1075* (2013.01); *B29L 2031/7543* (2013.01)

(56) References Cited

U.S. PATENT DOCUMENTS

| | | | |
|---|---|---|---|
| 6,258,099 | B1 | 7/2001 | Mareiro et al. |
| 6,786,889 | B1 | 9/2004 | Musbach et al. |
| 7,828,766 | B2 | 11/2010 | Durcan |
| 2001/0039395 | A1 | 11/2001 | Mareiro et al. |
| 2003/0004535 | A1 | 1/2003 | Musbach et al. |
| 2003/0055447 | A1 | 3/2003 | Lee et al. |
| 2003/0114915 | A1 | 6/2003 | Mareiro et al. |
| 2006/0030835 | A1 | 2/2006 | Sherman et al. |
| 2006/0085022 | A1* | 4/2006 | Hayes .............. A61M 25/104 606/192 |
| 2008/0300666 | A1 | 12/2008 | Heidner et al. |
| 2009/0299450 | A1 | 1/2009 | Nakamura et al. |
| 2010/0036314 | A1 | 2/2010 | Burton et al. |
| 2010/0130925 | A1 | 5/2010 | Haslinger |
| 2010/0130926 | A1 | 5/2010 | Lee et al. |
| 2010/0158193 | A1 | 6/2010 | Bates |
| 2010/0262218 | A1 | 10/2010 | Deshmukh |
| 2011/0022152 | A1 | 1/2011 | Grandt |
| 2012/0065718 | A1 | 3/2012 | Simpson et al. |
| 2014/0276401 | A1 | 9/2014 | Lee et al. |

OTHER PUBLICATIONS

International Search Report for corresponding PCT Application No. PCT/IB2013/052470, dated Aug. 13, 2013, 2 pages.
EMS-Grivory, EMS-Grivory Grivroy TR55 Transparent Nylon 12, Dry As Molded, (see http:/www.matweb.com/search/datasheet_print.aspx?matguid=d9ad606e69bb46a2aa5t80aa47cd0a4f), Nov. 18, 2015.

* cited by examiner

MEDICAL BALLOON

CROSS-REFERENCE TO RELATED APPLICATIONS

This application is a Continuation under 35 U.S.C. § 120 of U.S. patent application Ser. No. 13/794,972, filed Mar. 12, 2013, which claims priority to GB application no. 1205369.0, filed Mar. 27, 2012, titled "Method of Making a Medical Balloon," the contents of each of which are incorporated herein by reference in their entirety.

TECHNICAL FIELD

The present invention relates to a method of making a medical balloon, to a medical balloon and to a balloon catheter including such a balloon.

BACKGROUND ART

Medical balloons are used for a variety of medical procedures including angioplasty, scoring, vessel dilatation, valvuloplasty, occlusion, and for many other applications. In many such applications, it is desirable to provide additional components to tailor the balloon to improve its function in each of the various specific uses. One common procedure involving the use of a balloon catheter relates to angioplasty dilation of coronary or other arteries suffering from stenosis (that is, a narrowing of the arterial lumen which restricts blood flow). In angioplasty techniques the proper dilation of stenosed regions that are hardened and/or have become calcified can be difficult with a standard medical balloon. Therefore it is known to fix cutting elements, such as blades, onto the surface of the balloon in order to cut away at plaque and other build-up on the interior walls of a lumen. The blades may be fixed to the balloon with a layer of adhesive in a process can be fiddly and time consuming.

Often the manufacture of medical balloons is a complex and time consuming task, particularly having regard to the importance for reliability of the device.

Medical balloons are disclosed in a number of earlier publications including, for example, in US 2010/0036314, U.S. Pat. No. 6,143,416, U.S. Pat. No. 6,786,889, US 2009/0299450, U.S. Pat. No. 5,620,649, U.S. Pat. No. 7,828,766 and US 2010/0262218.

DISCLOSURE OF THE INVENTION

The present invention seeks to provide an improved method of making a medical balloon and an improved medical balloon and balloon catheter.

According to an aspect of the present invention there is provided a method of forming a medical balloon provided with a first layer made from a first material and a second layer made from a second material, said first and second layers being in overlying relationship with one another and integral with one another, wherein the first material has a softening or melting temperature which is higher than a softening or melting temperature of the second material; the method including the steps of: providing first and second layers of raw tubing made of said first and second materials respectively; locating said raw tubing in a mold; preheating the raw tubing to a preheat temperature and inflating the raw tubing so as to cause it to expand; heating the raw tubing to a first heat set temperature being the heat set temperature of the first layer and greater than the heat set temperature of the second layer, wherein at said preheat temperature the second layer is softened or molten, and/or wherein at said first heat set temperature the second layer is softened or molten, and/or wherein in the range between the heat set temperature and the preheat temperature the second layer is softened or molten; setting the inflated raw tubing to form the medical balloon; and cooling the set balloon.

In preferred embodiments the second layer is molten at the preheat temperature and/or at the first heat set temperature and/or in the range between the heat set temperature and the preheat temperature.

The method may include the step of incorporating a feature or component into the second layer. For example the method may comprise the step of applying texture to the second layer, in particular to an outer surface of the second layer.

The method may include the steps of providing adjacent the second layer at least one component and pressing the at least one component into the second layer such that the at least one component becomes at least partially embedded in the second layer. The at least one component may become fully embedded in the second layer.

Preferably the method provides a single stage process for forming a medical balloon, in particular for incorporating a feature or component into a medical balloon. The process can be faster and simpler than known methods for producing medical balloons.

The raw tubing may be a single tube having first and second layers integral with one another. The raw tubing may comprise two separate raw tubing layers. The two separate raw tubing layers may be held closely adjacent to one another. The second layer may be an outer layer of the raw tubing. The first layer may be an inner layer of the raw tubing.

The preheating step may heat the raw tubing to around 100 degrees centigrade.

The first heat set temperature may be in the region of 130 to 150 degrees centigrade. The first heat set temperature may be in the region of 140 to 150 degrees centigrade. The first heat set temperature may be the optimum heat set temperature of the first material.

According to another aspect of the present invention, there is provided a medical balloon for a balloon catheter, which balloon has at least a first layer made from a first material and a second layer made from a second material, said first and second layers being in overlying relationship with one another and being integral with one another; wherein the first layer has a softening or melting temperature which is higher than a softening or melting temperature of the second layer.

The first layer may act as a support for the second layer. The first layer may support the second layer at all times, even during manufacture of the balloon from raw tubing. By provision of the supporting first layer the balloon can be adapted to include an additional feature or component in the second layer without compromising the physical characteristics of the balloon, such as its strength or integrity. Even if the second layer loses strength or integrity, for example during manufacture, the balloon can maintain the characteristics required to perform its function by virtue of the presence of the first layer.

The first layer may be made from polyamide, polyether block amide, polyurethane, polyethylene, polyethylene terephthalate (PET) or silicone. The polyamide may be Nylon. The polyether block amide may be PEBAX™. The second layer may be made from the same material as the first layer, treated to have a lower softening or melting temperature than that of the first layer. The second layer may be made from any material having a lower melting temperature than the first layer. For example the second layer may be made from a resin, such as a functionalized polyolefin resin or a polyurethane resin. Examples of suitable materials for the second layer include an anhydride-modified ethylene elastomer based adhesive resin (such as Admer® SF755A), an anhydride-modified linear low density polyethylene (such as Plexar® PX3236 or a polyolefin modified with functional chemical groups to render it more hydrophilic. The second layer may be an amorphous polymer. In an embodiment the second layer is non-elastomeric. In an embodiment, both layers are thermoplastic elastomers. The inner layer may be a polyurethane that may be unmodified. The outer layer may be a polyolefin, which may be modified with hydroxyl groups or modified with anhydride groups.

The second layer may be softened or melted at or above a preheat or first processing temperature of the first layer. By preheat or first processing temperature it is meant a temperature at which the first layer can be stretched. The preheat or first processing temperature may be the temperature to which the balloon is heated to in a preheat step. The preheat or first processing temperature may be, for example, 100 degrees centigrade. The melting temperature of the second layer may be under 100° C., under 120° C. or under 140° C. The preferred melting temperature of the second layer may be in the range of 115 to 125 degrees centigrade. In an embodiment, the melting temperature of the first layer may be in the range of about 165 to about 205 degrees centigrade.

The first layer may have a heat set temperature above which the first layer is heat set. The second layer may have a heat set temperature above which the second material is heat set. The second layer may have a heat set temperature which is less that the heat set temperature of the first layer. When a material is heated to its heat set temperature whilst it is stretched, for example by inflation of the balloon, the material becomes fixed such that when inflation pressure is removed from the balloon the material maintains its size and form, rather than returning to its pre-inflated size and form. It is believed that at the heat set temperature the molecules of the material are substantially locked into their orientations such that on cooling the molecules do not return to any orientation they may have had before heat setting.

A balloon may be stretched and heated below the heat set temperature and on cooling may return, or at least partially return, to its pre-stretched and pre heated form. Heating a material to its heat set temperature may reduce, in particular minimize, shrinkage of the balloon on cooling after heating. Heating a balloon material to its heat set temperature may also increase the burst strength of the balloon. Heating a balloon material to a temperature above its heat set temperature may result in loss of burst strength compared to the burst strength of the balloon after heating only to its heat set temperature and then cooling. Heating a material to a temperature higher than its heat set temperature may overheat the material. By over-heating the balloon material it may lose at least some of its strength, possibly as a result in breakage of the polymer chains of the material. For example the second layer may lose its burst strength by heating it to the heat-set temperature of the first layer.

The first layer may have a heat set temperature between around 130 to 150 degrees centigrade, 140 to 150 degrees centigrade, or 145 to 150 degrees centigrade. The heat set temperature of the outer layer may be less than about 140 degrees centigrade. In embodiments it may be less than about 100 degrees centigrade. The second layer may have a heat set temperature of around 55 to 70 degrees centigrade. The second layer may have a heat set temperature of around 50 to 60 degrees centigrade. The second layer may have a heat set temperature which is at least 80, 70, 60, 50, 40 or 30 degrees centigrade less than the heat set temperature of the first layer. The second layer may have a heat set temperature which is at least 20 degrees centigrade less than the heat set temperature of the first layer. The second layer may have a heat set temperature which is at least 10 degrees centigrade less than the heat set temperature of the first layer. The second layer may have a heat set temperature which is no more than around 80% of the heat set temperature of the first layer.

Where the heat set temperature is a temperature range, the first layer may have an optimum heat set temperature within the heat set temperature range. Heating the balloon to the optimum heat set temperature of the first layer may result in a balloon for which shrinkage is minimized and burst strength is maximized.

Due to the relative hardness of the two layers, the first layer may provide a harder support for the second layer.

The first layer may have a thickness in the range from 0.01 millimeters to 0.05 millimeters. The first layer may have a thickness in the range from 0.02 millimeters to 0.04 millimeters. The second layer may have a thickness in the range from 0.003 millimeters to 0.02 millimeters. The second layer may have a thickness which is no more than 20% of a thickness of the first layer. The second layer may have a thickness which is no more than 40% of a thickness of the first layer.

In embodiments the thickness of the second layer may be equal to the thickness of the first layer. For example the second layer may have a thickness in the range from 0.01 millimeters to 0.05 millimeters. In other embodiments the thickness of the second layer may be greater than the thickness of the first layer. For example the second layer may have a thickness of up to 0.2 mm. A thicker second layer may be provided so as to enable elements to be at least partially embedded into the second layer.

The thickness of the first layer of the balloon may be chosen so as to provide the desired physical characteristics of the balloon. The physical characteristics of the balloon, such as burst strength, compliance and shape may be substantially determined by the first layer. The second layer may have no significant influence on such characteristics of the balloon. The first layer of the balloon may have a thickness equal to that of a single layer balloon exhibiting the desired physical characteristics of the balloon.

Preferably the burst strength of the inner layer is higher than the burst strength of outer layer.

The medical balloon may include at least one feature or component in the second layer. The second layer preferably has sufficient thickness such that an additional component may be securely embedded in the second layer, or sufficient thickness such that an additional feature may be provided in the second layer. An additional component may be partially or completely embedded in the second layer. The second layer may be relatively thick, for example it may be thicker than adhesive layers which have been used to bind additional components to balloons in existing products. As such additional components may be incorporated into a balloon of a balloon catheter more securely and more easily.

The first layer may be an inner layer and the second layer may be the outer layer of the balloon. The medical balloon may include at least one other layer integral with the first and second layers, the second layer being an outer layer of the balloon.

The medical balloon may include at least one component at least partially embedded in the second layer. The component may be or may include a strengthening sleeve, a woven material, a scoring element, a burst resist wire, a radiopaque marker, a cutting element, a high friction element, or a texturizing element. A texturizing element may for example be roughening particles which, when incorporated into the second layer, provide a roughened surface of the second layer. The additional component may tailor the features of the balloon, for example to improve the balloon's performance for a specific use. The additional component may be integral with the second layer of the balloon for example by being embedded in or incorporated into the second layer. The additional component may protrude beyond the surface of the second layer of the balloon, for example to provide a scoring surface.

The second layer may comprise a soft layer. By soft it is meant that the layer may deform around an element or device, such as a stent, pressed into it. The second layer may remain relatively soft after manufacture of the balloon such that an element or device may be partially embedded into the soft layer after manufacture of the balloon. For example, a stent may be crimped into the soft layer in order to attach it to the balloon. In this case the stent may be partially embedded in the soft layer. Where the second layer is a soft layer the second layer may be thicker than the first layer.

The second layer may comprise a high friction layer. For example the second layer may comprise a material which gives the surface of the second layer high friction.

The medical balloon may include at least one feature in the outer layer. For example the outer layer may be textured, such as roughened, or the outer layer may be a high friction layer.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

It is to be understood that the drawings are schematic only and are not intended to be representative of dimensions or proportions of the various elements shown therein. In some instances, dimensions, sizes and proportions have been modified in order to assist in the visualization of various features of the elements shown, that is for the purpose of explanation only. The person skilled in the art will be aware of the appropriate dimensions and proportions having regard to common knowledge in the art.

Figure 1:
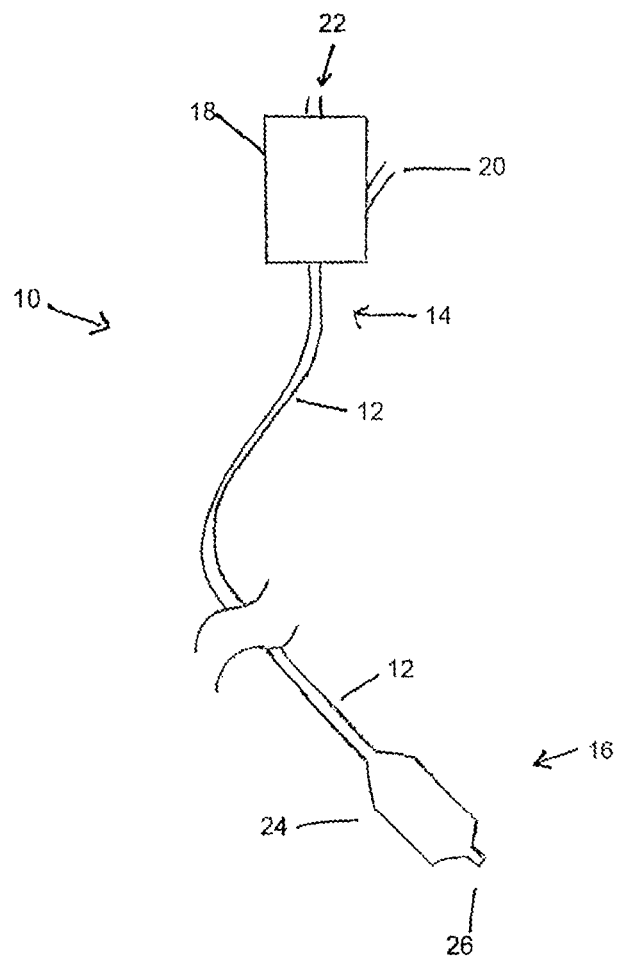
FIG. 1 is a schematic diagram of a balloon catheter.

Referring to FIG. 1, there is shown in schematic form the principal components of a balloon catheter assembly 10, which components are generally known in the art. The balloon catheter includes a catheter 12 having a proximal end 14 and a distal end 16. At the proximal end 14, the catheter is coupled to a manipulation unit and valve assembly 18, which typically includes one or more haemostatic valves (not shown), a port 20 for feeding flushing liquid into the catheter 12, typically saline solution, and a proximal cannula 22 for use, for example, in feeding a guide wire (not shown) through the catheter 12.

At the distal end 16 of the balloon catheter 10, there is provided a medical balloon 24. The balloon 24 may be used, for example, in an angioplasty or other vessel dilatation procedure, for valvuloplasty, for occlusion, or for any other procedure. The balloon 24 is typically wrappable around the catheter 12, the latter extending through the balloon 24 to the tip 26 of the assembly 10. The balloon is also inflatable, via an inflation lumen in the catheter 12, so as to attain a deployed, inflated configuration, as shown in FIG. 1. The balloon 24 may have a variety of shapes but typically may have a substantially cylindrical body portion bounded by conical end portions which themselves are bounded to neck portions which are fixed in fluid tight manner to the catheter 12.

Figure 2:
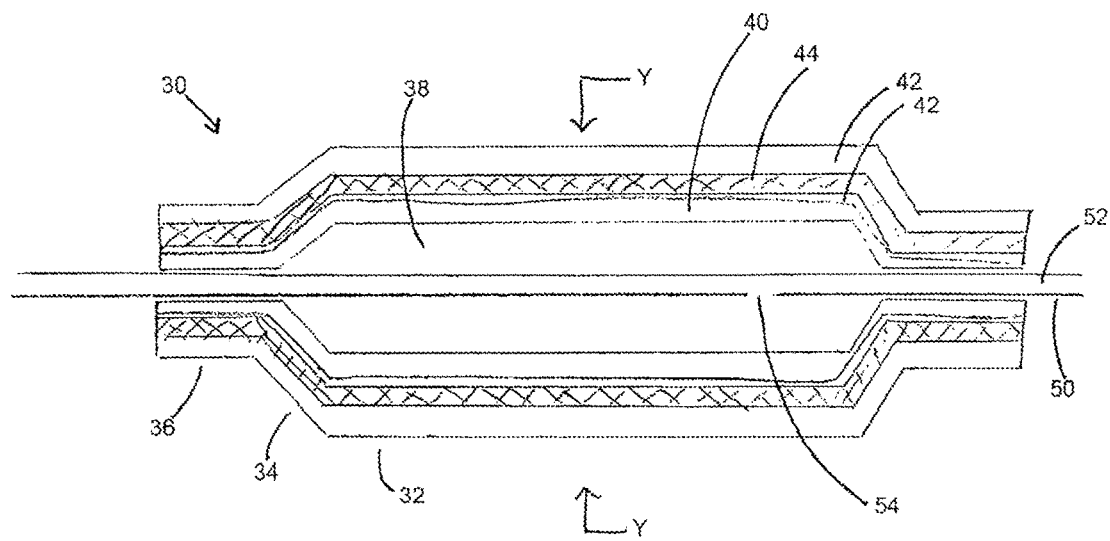
FIG. 2 is a cross-sectional sectional view of an embodiment of the medical balloon taught herein.
Figure 3:
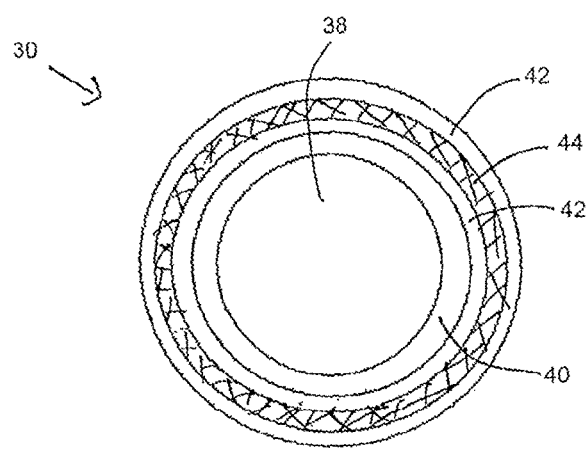
FIG. 3 is a cross-sectional view along Y-Y of the medical balloon of FIG. 2.

Referring now to FIGS. 2 and 3, there is shown a first embodiment of medical balloon 30 according to the teachings herein. The balloon 30 has a strengthening element 44 for strengthening the balloon. FIG. 2 is cross sectional view of a part of the balloon 30 taken along the longitudinal axis of the balloon. FIG. 3, on the other hand, is a view of the balloon 30 along its longitudinal axis. The balloon 30 has a body portion 32 which is substantially cylindrical. This is bounded by first and second conical ends 34 which in turn terminate at first and second necks 36 which are typically bonded or otherwise sealed to a catheter 50. It will be apparent, in particular from FIG. 2, that catheter 50 extends through the balloon 30 and is provided, typically, with an inflation lumen 52 which has a port 54 in communication with the internal chamber 38 of the balloon 30. Inflation lumen 52 is used to inflate and deflate the balloon 30 for deployment purposes, in a manner well known in the art.

As can be seen in FIG. 2, the balloon 30 is formed, of an inner layer 40 and an outer layer 42. Typically, the inner and outer layers 40, 42 have a substantially even thickness, although it is not excluded that they may have a non-uniform thickness. The outer layer is thick compared to, for example, a layer of adhesive, which may alternatively be used to bind an additional component to a balloon. The end cones 34 and/or the necks 36 may have a thickness which varies, for example as a result of the method of manufacture of the balloon.

The outer layer 42 is integral with or otherwise bonded to the inner layer 40. The structure of layers 40, 42 is such that when the balloon 30 is inflated, by means of inflation fluid fed through the lumen 54 of the catheter 50, the balloon 30 will unwrap from the catheter 50 and expand to its inflated condition shown in FIGS. 2 and 3.

The strengthening element 44 is fully embedded in the outer layer 42 of the balloon 30 such that it lies within the outer layer. The strengthening element may be embedded further into the balloon such that it lies substantially between the inner 40 and outer 42 layers of the balloon 30. In another embodiment the strengthening element may be partially embedded in the outer layer such that at least part of the strengthening element protrudes from the second layer.

In a preferred embodiment the strengthening element is a strengthening sleeve such as a braided or otherwise constructed mesh made from filamentary material. The filamentary material may be, for example, a metal wire. In one embodiment the strengthening element is a strengthening layer.

The inner layer 40 of the balloon 30 can be made of a variety of materials including, for example, polyamide (e.g. Nylon), polyether block amide (e.g. PEBAX™), polyethylene, polyurethane, silicone, polyethylene terephthalate (PET) or other suitable material. The heat set temperature for Nylon and PEBAX™ may be approximately 140-145 degrees centigrade. The outer layer 42 of the balloon could be made of similar materials or a different material than that of the inner layer 40, all being of a formulation having a lower softening or melting temperature than the material of the first balloon layer. The outer layer 42 is preferably made of a functionalized polyolefin resin or a polyurethane resin. Of course, either or both layers 40, 42 can be made from a plurality of compounds. The outer layer 42 may be formed from a polyolefin base material modified with functional chemical groups to make it more hydrophilic. Examples of suitable materials for the outer layer include an anhydride-modified ethylene elastomer based adhesive resin (such as Admer® SF755A) or an anhydride-modified linear low density polyethylene (such as Plexar® PX3236).

In a preferred embodiment the physical characteristics of the balloon, such as burst strength, compliance and shape is substantially determined by the inner layer. Preferably the outer layer has no significant influence on such characteristics of the balloon. Therefore, the thickness of the inner layer is preferably equal to the thickness of a single layer balloon with the desired physical characteristics of the medical balloon. The inner layer provides a support for the outer layer at all stages of manufacture, allowing the properties and characteristics of the outer layer to change without compromising the physical characteristics of the balloon.

The balloon could be non-compliant, semi-compliant or compliant in dependence upon the medical application. The compliance of the inner layer 40 can be determined by a number of factors, including the material used, the nature of that material, the thicknesses of the layer and so on. These are all parameters which a person skilled in the art will be able to ascertain on the basis of common general knowledge.

It is to be appreciated that the strengthening element 44 is just one example of an additional component or feature which may be incorporated into a medical balloon for use in medical procedures. The teachings herein, particularly in connection with the method of manufacture of the balloon described below, allow for a large variety of different additional components to be incorporated into a medical balloon.

Figure 4:
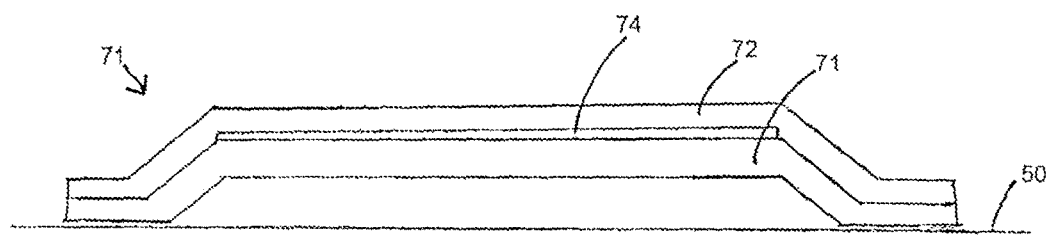
FIG. 4 is a cross-sectional sectional view of another embodiment of the medical balloon.
Figure 5:
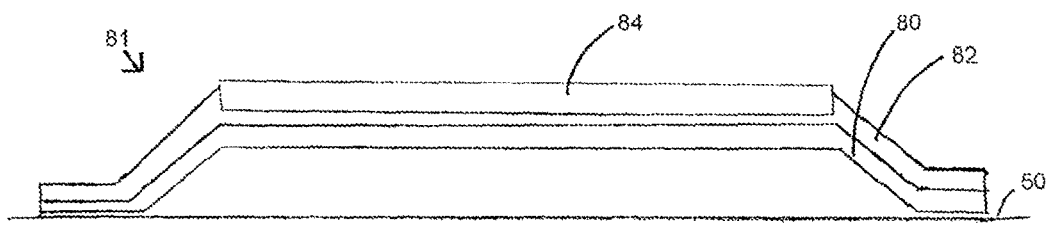
FIG. 5 is a cross-sectional view of yet another embodiment of the medical balloon.

Some examples are given in FIGS. 4 and 5, to which reference is now made. All of these Figures show cross-sectional views of different examples of medical balloon.

In FIG. 4, a radiopaque element 74 is embedded so as to lie substantially between the inner 70 and outer 72 layers of the balloon 71. As with the previously described embodiments, the balloon 71 includes inner and outer layers 70, 72 of the type disclosed herein. The radiopaque element is made from radiopaque material such as, for example, palladium, silver and other radiopaque materials known to the skilled person.

In a preferred embodiment the radiopaque element is a radiopaque layer. In other embodiments the radiopaque element maybe a radiopaque marker-block.

As described previously with reference to other additional components incorporated into the balloon, in other embodiments the radiopaque element may be embedded within the outer layer so that it is surrounded by the outer layer, or partially embedded in the outer layer such that it extends from the outer layer.

FIG. 5 shows a view of another example of a medical balloon 81 along its longitudinal axis. The balloon 81 comprises a plurality of scoring elements 84 which extend longitudinally along the length of the balloon. The scoring elements, which may be thin wires or fibers 84, are stiffer than the balloon wall so that they can score into the wall of the vessel in which the balloon is inflated. The scoring elements may comprise a plastic polymer material, or a metal or metal alloy, such as Kevlar for example. The scoring elements 84 are embedded in the outer layer 82 of the balloon 81 and protrude above the circular perimeter of the balloon so as to be able to interact with the wall of the lumen in which the balloon 81 is placed. In the embodiment shown in FIG. 5 the scoring elements 84 extend along the main body part of the balloon only, not along the narrower end cone and neck portions of the balloon. The balloon 80 has inner and outer layers 80, 82 of the characteristics taught herein.

The additional components described with reference to the Figures could be used individually or in combination with one another. The components may be arranged about any particular portion of the balloon, or about the entire balloon.

The structure of the balloon and its method of manufacture, described below, allows for the provision of medical balloons having a variety of additional components such that the specific characteristics of the balloon can be tailored for a particular medical application.

There follows a description of a preferred embodiment of manufacturing a balloon having characteristics of the type disclosed herein.

Figure 6:
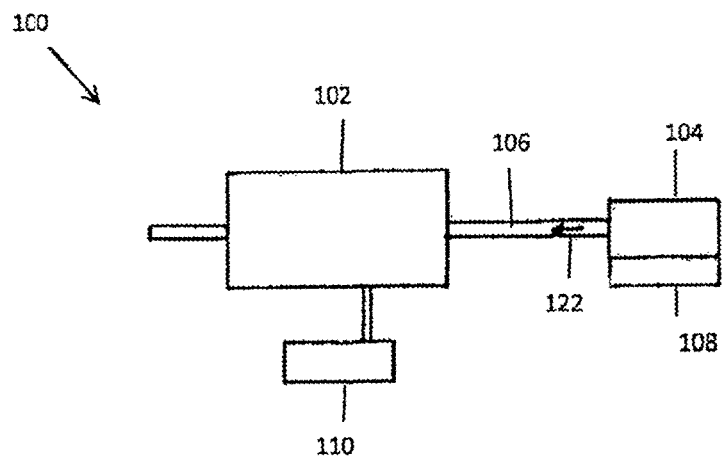
FIG. 6 is a schematic view of an embodiment of assembly for use in the manufacture of medical balloon and balloon catheters of the types disclosed herein.

Referring now to FIG. 6, there is shown in schematic form an embodiment of assembly 100 for use in the manufacture of medical balloon and balloon catheters of the types disclosed herein.

The assembly 100 includes a mold 102, a pumping unit 104 for pumping inflation fluid through a conduit 106 into the mold 102 and specifically into a raw tubing from which the medical balloon is formed as described in further detail below. The pumping unit 104 may be provided with a heater 108 for heating the pumping fluid to various temperatures. There may be provided a separate heating unit 110 for heating the mold 102 during the process of fabrication of a medical balloon.

Figure 7:
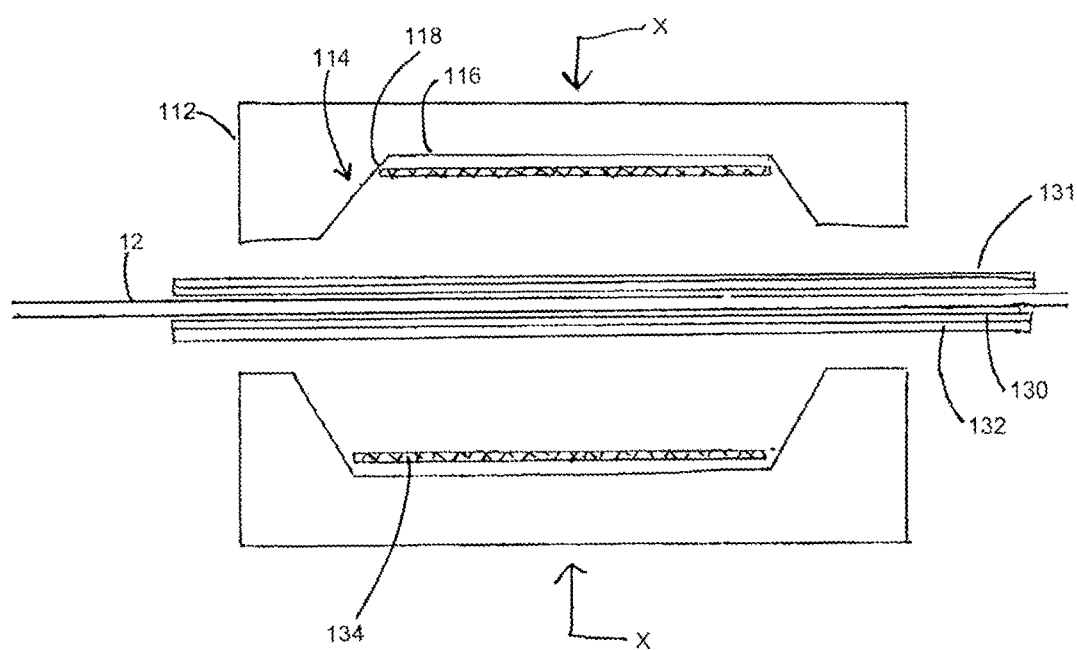
FIG. 7 is a cross-sectional view of an embodiment of the raw tubing for a medical balloon positioned inside a mold, for manufacturing a medical balloon as taught herein.
Figure 8:
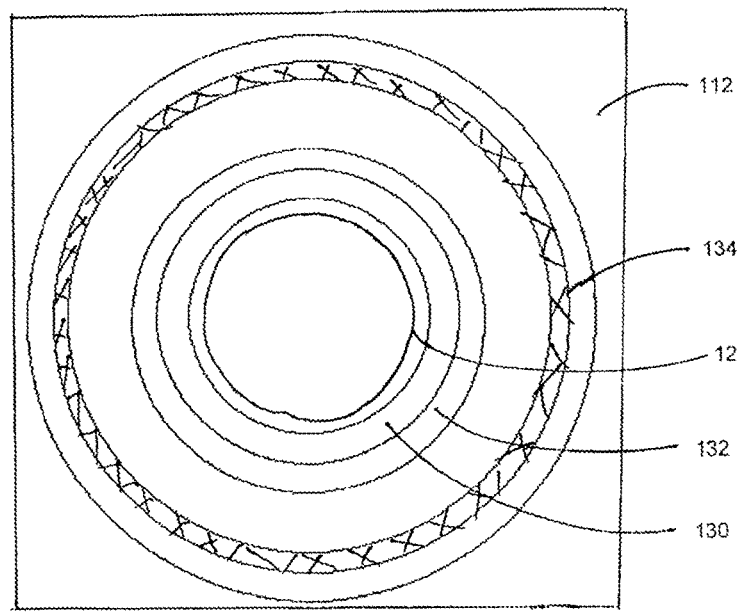
FIG. 8 is a cross-sectional view along X-X of the raw tubing and mold of FIG. 7.

In FIG. 7 there is shown a cross-sectional view of an embodiment of the raw tubing 131 for a medical balloon positioned inside a mold 112 shaped to produce a medical balloon having a strengthening element 134 incorporated into it. FIG. 8 shows a cross-sectional view along X-X of the raw tubing and mold of FIG. 7. The mold 112 has an internal wall 114 with a substantially cylindrical surface 116 bounded by tapering sections 118 which in practice will form the end cones 34 of the balloon.

A strengthening sleeve is located in the mold between the raw tubing and the mold but not attached to either the mold or the tubing before the balloon is heated and expanded to incorporate the strengthening sleeve.

In the example of FIG. 7, the mold 112 is longitudinally divided in at least two portions forming half a mold each. The structure of the mold 112 is not, however, relevant to the disclosure herein in that the mold 112 could have sections divided in other ways, for example transversally rather than longitudinally, in order to gain access to the inside of the mold for the purposes of removing a balloon formed therewithin.

Where the additional component is a strengthening wire, or a scoring element, for example, longitudinal grooves (not shown) may be provided within the substantially cylindrical portion 116 of the mold in order to provide a support for the strengthening wires or scoring elements. The longitudinal grooves may extend longitudinally along inside surface of the cylindrical portion 116. The grooves can support the additional components before they are incorporated into the outer layer of the balloon in the balloon forming process. In another embodiment the additional components may be lightly attached to the mold or the tubing so as to support them in a desired position relative to the raw tubing 131.

The raw tubing 131, of the type used in making a medical balloon of any of the types disclosed herein, is located within the mold 112. The raw tubing 131 is formed, for example by co-extrusion, of two layers 130 and 132. The inner layer 130 forms the inner layer 40, 70, 80 of the balloon, whereas the outer layer 132 forms the outer layer 42, 72, 82 of the balloon. These layers are thus made of the same material as the eventual layers of the balloon.

In practice, the raw tubing 131 is fed into the mold 12, typically in the direction of the arrow 122 shown in FIG. 7 so as to extend into and through the mold 12. Once so fed, the raw tubing 131 is suitably clamped into the mold and closed off at its extreme end. The fixing is such as to seal the end in fluid tight manner. This arrangement is known in the art and will thus be immediately evident to the skilled person.

The tubing 131, which is typically a very long or continuous length of tubing, is cut to an appropriate length and then coupled to the conduit 106, in a known manner. In practice, the conduit 106 may form a balloon catheter 12, in which case the raw tubing 131 would be fixed over the catheter after having been cut to size with its two ends sealed to the catheter 12 at locations which would form the necks 36 of the balloon.

The mold 112 is heated to a preheat temperature, such as, for example, 100 degrees centigrade. Additionally, fluid pressure, typically also heated, is fed by means of the pump (104 shown in FIG. 6) into the raw tubing 131. The heat applied to the raw tubing causes the inner layer 130 of the raw tubing to soften slightly and allows it to stretch when the pressure of the inflation fluid pushes against it, such that the raw tubing can expand within the chamber of the mold 112. The raw tubing 131 is expanded towards the internal wall 114 of the mold 112, and the outer layer 132 is eventually pressed against these walls and against the strengthening element 134 by continuing inflation pressure.

Once the tubing 131 has been preheated and expanded to push against the wall 114 of the mold 112 the temperature of the mold 112 is increased so as to heat the inner layer 130 to its optimum heat set temperature.

At or above the preheat temperature the outer layer 132 of the balloon is softened more than the inner layer such that it is able to flow. As the outer layer 132 is able to flow, when the outer layer 132 is pushed against any additional component present in the mold the outer layer 132 is displaced around said additional component and the additional component is forced into the outer layer 132. As the inner layer 130 remains more solid and is not able to flow, the inner layer is not displaced around the additional component; the additional component does not to penetrate the inner layer.

The outer layer of the tubing may be displaced around the additional component to varying extents, for example, only slightly so as to partially embed the additional component in the surface of the outer layer, or more substantially so as to fully embed the additional element in the outer layer. The extent may depend on the thickness of the outer layer, the thickness of the additional element, and the temperature to which the tubing is heated in the preheat step. In the embodiment shown in FIGS. 7 and 8, where the additional component is a strengthening element, it is desired that the strengthening element be completely embedded in the outer layer of the balloon.

Both the inner and outer layers 130,132 of the balloons are heat-set at the heat set temperature of the inner layer. The inner layer is set so as to fix the bonds between the molecules in the expanded tube configuration and to substantially prevent shrinkage on cooling. The outer layer is also set so as to set the bonds between the molecules in the expanded tube configuration.

Figure 9:
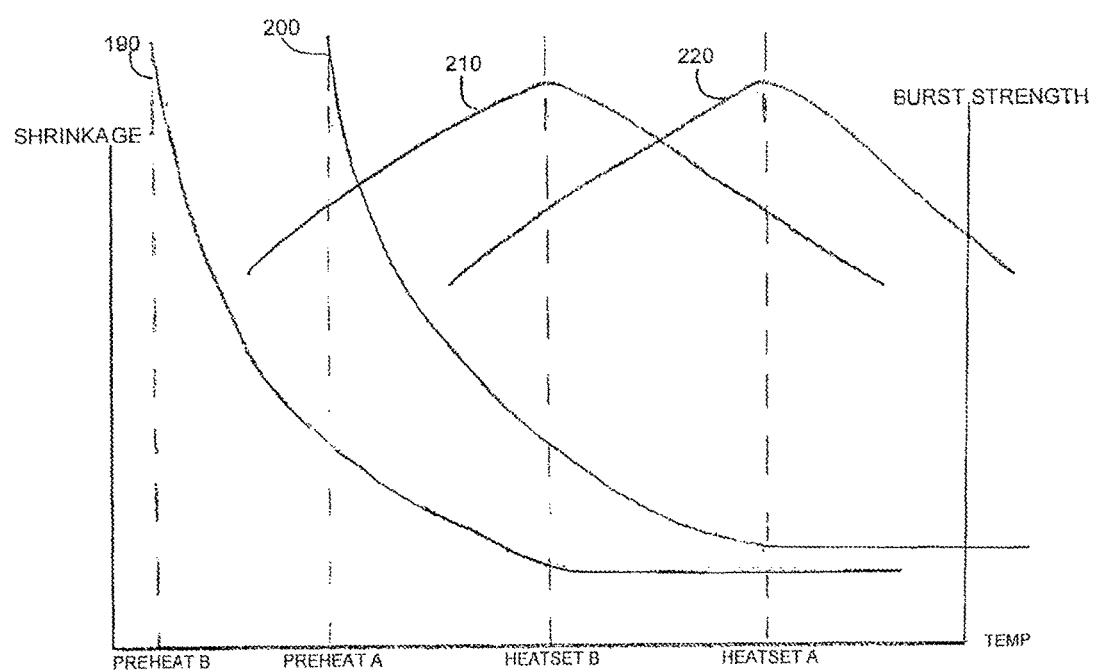
FIG. 9 is a graph depicting the shrinkage and burst strength of the inner and outer layers of balloon material as they vary with temperature.

FIG. 9 is a graph depicting the shrinkage of the inner 200 and outer 190 layers and the burst strength of the inner 220 and outer 210 layers of balloon material as they vary with temperature.

The graph shows that as temperature is increased to a materials heat set temperature (Heat set A and plot 220 for the inner layer and Heat set B and plot 210 for the outer layer) the burst strength of that material rises, only to fall again on heating to above the heat set temperature. The graph also shows that as the temperature is increased above the heat set temperature the shrinkage of the balloon is dramatically reduced (when cooled after heating).

The graph also shows that once the material is heated to its heat set temperature, heating over that heat set temperature does not continue to reduce shrinkage on cooling. There is a preferred point therefore for each material at the heat set temperature where shrinkage is minimized and burst strength is maximized.

As can been seen from the graph, heating the outer layer to the heat set temperature of the inner layer, which heats the outer layer to a temperature above its own heat set temperature, results in a decrease in burst strength of the outer layer. This is possibly caused by breakage of the polymer chains of the material.

However, this does not compromise the strength or burst strength of the balloon as the inner layer maintains its strength and provides the physical characteristics of the balloon.

Once the balloon has been heat set, the mold 112 is cooled or allowed to cool. On cooling the additional components are fixed into the outer layer of the balloon and thus incorporated into the balloon. The mold 112 is preferably cooled to substantially ambient temperature, and the balloon then removed from the mold. Typically, this can be achieved by deflating the balloon so as to facilitate its retraction form the mold surfaces.

The provision of two layers to the balloon integral with one another enables the reflow, molten or softened outer layer to be supported by the more solid inner layer upon heating and inflation of the balloon. As such the outer layer can be changed structurally so as to incorporate additional components or features into the balloon, whilst the inner layer maintains the physical characteristics required by the balloon such as burst strength and compliance. In such a way additional components may be incorporated into a balloon in an easy and effective way without compromising the physical characteristics of the balloon. The inner layer acts to provide support to the outer layer, both during the manufacture of the balloon and also during subsequent deployment of the balloon in a medical procedure.

In some embodiments the second layer of the balloon comprises a soft layer. By soft it is meant that the layer may deform around an element or device, such as a stent, pressed into it. The second layer remains relatively soft after manufacture of the balloon such that an element or device may be partially embedded into the soft layer after manufacture of the balloon. In one embodiment, a stent is crimped into the soft layer, partially embedding the stent into the soft layer and thus attaching the stent to the balloon. The soft layer is thicker than the first layer in order to provide sufficient thickness for the stent to partially embed. For example, the soft layer may have a thickness substantially equal to the thickness of the stent strut.

The skilled person would appreciate that modifications could be made to the above-described embodiments. Any compatible materials could be used for the two layers (for example, two hydrophobic layers or two hydrophilic layers), as long at the material for the inner layer has a higher melting temperature than that of the outer layer. Furthermore, it would be possible to combine a hydrophilic layer with a hydrophobic layer by chemically linking the layers or including a middle "tie" layer with intermediate properties.

The preferred embodiments have only two balloon layers, the layers having been preferably co-extruded to form the raw tubing used to form the balloon, or otherwise bonded to one another so as to be integral with one-another. Other embodiments contemplate more than two layers, for example, three or more, with the proviso that the outer layer of the balloon remains supported by an internal layer which does not melt or flow so as to incorporate additional components at the processing temperatures. In some embodiments the raw tubing may comprise two separate layers, each layer being a separate raw tube. The two separate raw tubes may be provided one inside the other, closely adjacent to one another.

Although the claims are set in single dependent form, it is to be understood that the features of the dependent claims can be combined with one another in accordance with the teachings above, as if the claims were in multiple dependent form.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in United Kingdom patent application number GB 1205369.0, from which this application claims priority, and in the abstract accompanying this application are incorporated herein by reference.

We claim:

1. A method of making a balloon, so that said balloon comprises:
    an inner layer comprising a first expandable material having a first softening or melting temperature;
    an outer layer comprising a second expandable material including a functionalized polymer, and having a second softening or melting temperature that is lower than the first softening or melting temperature;
    wherein the inner and outer layers are disposed in an overlying and integral or otherwise bonded relationship with one another; and
    a woven material or braided mesh that is at least partially embedded in the outer layer;
    wherein the inner layer has a heat-set temperature higher than a heat-set temperature of the outer layer, and the inner layer is free of the woven material or braided mesh
    and
    wherein the method of making the balloon comprises steps of:
    placing the woven material or braided mesh within a mold comprising a cavity defined by an internal cylindrical surface;
    directing a portion of the inner layer and the outer layer, formed as raw tubing, into the cavity;
    preheating the raw tubing to a temperature, at or above the second softening or melting temperature and below the first softening or melting temperature, such the outer layer is softened to be flowable and the inner layer is soft enough to be expanded, and
    expanding, by fluid pressure, the portion of the raw tubing within the cavity such that the expanding places the softened outer layer into contact with the woven material or braided mesh and where the softened outer layer is forced flowably into and at least partially through the woven material or braided mesh so as to at least partially embed the woven material in the outer layer.

2. The method of claim 1, further comprising a step of further heating to a heat-set temperature of the first expandable material of the inner layer.

3. The method of claim 2, where the step of expanding within the cavity and the further step of heating to the heat-set temperature of the first expandable material of the inner layer provides a burst strength of the inner layer that is higher than a burst strength of the outer layer.

4. The method of claim 1, further comprising a step of cooling, wherein the woven material or braided mesh is fixed in the outer layer.

5. The method of claim 1, where the functionalized polymer comprises a functionalized polyolefin, and the first expandable material comprises nylon.

6. The method of claim 1, where the outer layer comprises material selected from a group consisting of polyolefin resin, polyurethane resin, anhydride-modified ethylene elastomer-based adhesive resin, anhydride-modified linear low-density polyethylene, a polyolefin modified with hydroxyl groups, a polyolefin modified with anhydride groups.

7. The method of claim 1, where the second softening or melting temperature is in a range selected from 115° C. to 140° C., 115° C. to 125° C., below 100° C., below 120° C., and below 140° C.

8. The method of claim 1, where a thickness of the outer layer is in a range selected from no more than 20% of a thickness of the inner layer and no more than 40% of a thickness of the inner layer.

9. The method of claim 1, where the first softening or melting temperature is in a range from 165° C. to 205° C.

10. The method of claim 1, where the heat-set temperature of the outer layer is no more than about 80% of the heat-set temperature of the inner layer.

11. The method of claim 1, where the heat-set temperature of the outer layer is at least 20° C. less than the heat-set temperature of the inner layer, or is at least 10° C. less than the heat-set temperature of the inner layer.

12. The method of claim 1, where the inner layer comprises a material selected from a polyamide, a polyether block amide, a polyurethane, a polyethylene, polyethylene terephthalate (PET), and silicone.

13. A medical balloon comprising:
- an inner layer comprising a first expandable material having a first softening or melting temperature;
- an outer layer comprising a second expandable material having a second softening or melting temperature that is lower than the first softening or melting temperature;
- wherein the inner and outer layers are disposed in an overlying relationship with one another combined by a middle tie layer with a melting temperature intermediate of inner layer melting temperature and outer layer melting temperature; and
- a woven material that is at least partially embedded in the outer layer;
- wherein the inner layer has a heat-set temperature higher than a heat-set temperature of the outer layer, and the inner layer is free of the woven material.

* * * * *